United States Patent [19]

Gupta et al.

[11] 4,262,198

[45] Apr. 14, 1981

[54] BROADBAND OPTICAL RADIATION DETECTOR

[75] Inventors: Amitava Gupta, Pasadena; Su-Don Hong, Temple City; Jovan Moacanin, Los Angeles, all of Calif.

[73] Assignee: California Institute of Technology, Pasadena, Calif.

[21] Appl. No.: 61,822

[22] Filed: Jul. 30, 1979

[51] Int. Cl.³ .................... G01J 1/00; H01J 31/50
[52] U.S. Cl. .................... 250/340; 250/227; 250/332; 250/350; 250/351; 350/353
[58] Field of Search ............ 250/330, 472, 316.1, 250/332, 227, 342, 349, 350, 351, 474, 340; 350/360, 361, 359, 96.15, 363, 354, 353; 346/77 E

[56] References Cited

U.S. PATENT DOCUMENTS

| | | | |
|---|---|---|---|
| 2,824,235 | 2/1958 | Hahn et al. | 250/351 |
| 3,106,642 | 10/1963 | Shapiro | 250/350 |
| 3,130,309 | 4/1964 | Snyder | 250/330 |
| 3,265,892 | 8/1966 | Sheldon | 250/227 |
| 3,311,749 | 3/1967 | Briggs | 250/227 |
| 3,397,313 | 8/1968 | Mast | 350/361 |
| 3,434,779 | 3/1969 | Damen et al. | 350/353 |
| 3,552,824 | 1/1971 | Kiss | 350/354 |
| 3,672,221 | 6/1972 | Weil | 350/353 |
| 4,160,907 | 7/1979 | Bly | 250/330 |

OTHER PUBLICATIONS

Lynch, "Fiber Optic Connector", IBM Tech. Disclosure Bulletin, vol. 13, No. 2, 7-70, 533-534.
Gershon-Cohen, "Medical Thermography", Scientific American, vol. 216, No. 2, 2-67, pp. 94-102.

*Primary Examiner*—Alfred E. Smith
*Assistant Examiner*—Carolyn E. Fields
*Attorney, Agent, or Firm*—Freilich, Hornbaker, Wasserman, Rosen & Fernandez

[57] ABSTRACT

A method and apparatus for detecting optical radiation by optically monitoring temperature changes in a microvolume caused by absorption of optical radiation to be detected. More specifically, a thermal lens-forming material is provided which has first and second opposite, substantially parallel surfaces. A reflective coating is formed on the first surface, and a radiation-absorbing coating is formed on the reflective coating. Chopped, incoming optical radiation to be detected is directed to irradiate a small portion of the radiation-absorbing coating. Heat generated in this small area is conducted to the lens-forming material through the reflective coating, thereby raising the temperature of a small portion of the lens-forming material and causing a thermal lens to be formed therein. The thus-formed thermal lens is optically detected by irradiating the thermal lens by a collimated light beam. The light beam, after having passed through the thermal lens, is reflected by the reflective coating back through the thermal lens, and directed by a beam splitter to an optical detector. In a further embodiment of the invention, the optical radiation to be detected is passed through a template, thereby defining a plurality of areas on the radiation absorbing coating to be irradiated. A corresponding template is provided in a spread, collimated light beam to define a plurality of coherent light beams, each of which passes through a thermal lens in the lens-forming material. Each beam is then reflected by the reflective coating, passes back through the thermal lens, and is directed by a beam splitter to an optical detector. The invention is particularly useful as a broadband infrared detector.

26 Claims, 9 Drawing Figures

BROADBAND OPTICAL RADIATION DETECTOR

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

The invention relates to optical detectors or optical detector arrays, and more specifically to infrared detectors or detector arrays having high sensitivity and utilizing photothermal principles.

Optical detectors or detector arrays are typically of two types, the first type being based on photoelectric principles and the second type being based on thermal principles. The first type of optical detector includes photodiodes, photomultipliers, and the like. These detectors utilize quantum mechanical processes involving separation of charge due to absorption of a photon. The second type of optical detector includes pyroelectric detectors and thermistors. These detectors utilize all types of couplings in which a temperature change causes a direct change in voltage, resistance or capacitance.

There is a generally recognized need for a highly sensitive, broadband optical or infrared detector or detector array both in government and in industry. Utilizing conventional thermal detectors, high sensitivity can be achieved at certain wavelength ranges in the infrared region by using detectors operated at cryogenic temperatures, one example being a Ge-Cu detector which operates at 1.4° K. Alternatively, pyroelectric detectors can be utilized; however, these have reduced sensitivity and relatively flat wavelength response. There is a need today for optical detectors which have high sensitivity, broad wavelength responses, can be operated at room temperature (10°–40° C.) and can be easily fabricated into detector arrays. The optical detector provided by the invention meets these needs.

SUMMARY OF THE INVENTION

The present invention provides a broadband, optical radiation detector which incorporates a means for optically monitoring a volume element whose temperature has been increased due to absorption of optical radiation to be detected. The volume element is continuously irradiated by a collimated light beam and its intensity monitored after having passed through the volume element, the intensity being related to the characteristics of a thermal lens in the volume element.

In a specific embodiment, a lens-forming laminate is formed of a lens-forming material, one surface of which is coated with a reflective coating. The reflective coating in turn is coated with a radiation-absorbing coating, the lens forming material, reflective coating and radiation-absorbing coating all being in thermally conductive contact with each other. The radiation-absorbing coating is irradiated by optical radiation to be detected, the irradiation being continuously chopped so as to alternately heat and not heat the radiation-absorbing coating. The thermal energy created by the radiation to be detected is thermally conducted by the reflective coating to the lens-forming material, a small volume of which is heated so that a thermal lens is formed therein.

The thermal lens is dissipated during periods when the optical radiation is blocked from the radiation absorbing material. The thermal lens is continuously monitored by a collimated light beam or monitoring beam which is directed to the volume in which the thermal lens is formed. This beam is orthogonally directed with respect to the reflective coating. Portions of the light beam reflected by the reflective coating back through the thermal lens are provided to an optical detector by a beam splitter located in the collimated light beam. In another embodiment of the invention, a plurality of thermal lenses are formed by the optical radiation to be detected, and a plurality of optical detectors are provided to monitor the thermal lenses. Output signals from the detectors can be used to form a profile of the field of view of the optical radiation to be detected.

This contactless probing or monitoring of the volumes in which the thermal lenses are formed results in several advantages not achieved by conventional detectors. First, electrical noise which is limiting for pyroelectrical detectors is removed, thus eliminating tangent delta loss and Johnson noise. A surface area less than 0.1 square millimeter is sufficient for the volume to be monitored. Thus a very large element array can be concentrated in a small area. Sensitivity of the detector is extremely high since modulation of the probe beam can be determined with high precision. The invention is especially useful for detecting the infrared wavelength range between 0.85 and 24 microns for which conventional thermal detectors often require elaborate, costly and sometimes unreliable cooling means in order to achieve a desired detectivity.

DETAILED DESCRIPTION

Detailed illustrative embodiments are described herein which exemplify the invention and are currently considered to be the best embodiments for such purposes. However, it is to be recognized that other means for transmitting the optical radiation to be detected to the radiation-absorbing material, and other means for detecting the presence of thermal lenses in the lens-forming material could be utilized. Accordingly, the specific embodiments disclosed are representative in providing a basis for the claims which define the scope of the present invention.

As previously explained, the invention provides a broadband optical radiation detector which is extremely compact, has high sensitivity, and does not require an external cooling means. A thermal lens-forming laminate is provided which includes a lens-forming material in which a thermal lens can be formed and dissipated. A reflective coating deposited on one surface on the lens-forming material and a radiation-absorbing coating deposited on the reflective coating are provided. Optical radiation to be detected, which in specific applications of the invention could be infrared radiation having wavelengths longer than 0.85 microns, is directed at the radiation absorbing coating. The optical radiation to be detected is alternately blocked and unblocked so as to alternately heat and not heat a small portion of the radiation absorbing coating. Heat from the portion being irradiated is thermally conducted through the reflective coating to the lens forming material in which thermal lenses are alternately formed and dissipated. A collimated light beam is provided to monitor the thermal lens formed within the lens-forming material. This collimated light beam is orthogonally directed through the thermal lens to the reflective coating, and reflected therefrom back along the axis of the collimated light beam. A beam splitter is provided which reflects this reflected-back portion to an optical detector. In the absence of the thermal lens, the full strength of the beam impinges upon the optical detector, thereby causing it to provide a maximum output. However as a thermal lens is formed, the beam passing through it is broadened, thereby reducing the amount of light impinging upon the optical detector. This reduced amount of light causes the optical detector to provide a reduced output. AC coupling of the optical detector output to a monitoring means provides a signal whose amplitude is related to the magnitude of the thermal lens formed within the lens-forming material, and thus to the optical radiation to be detected.

Figure 1:
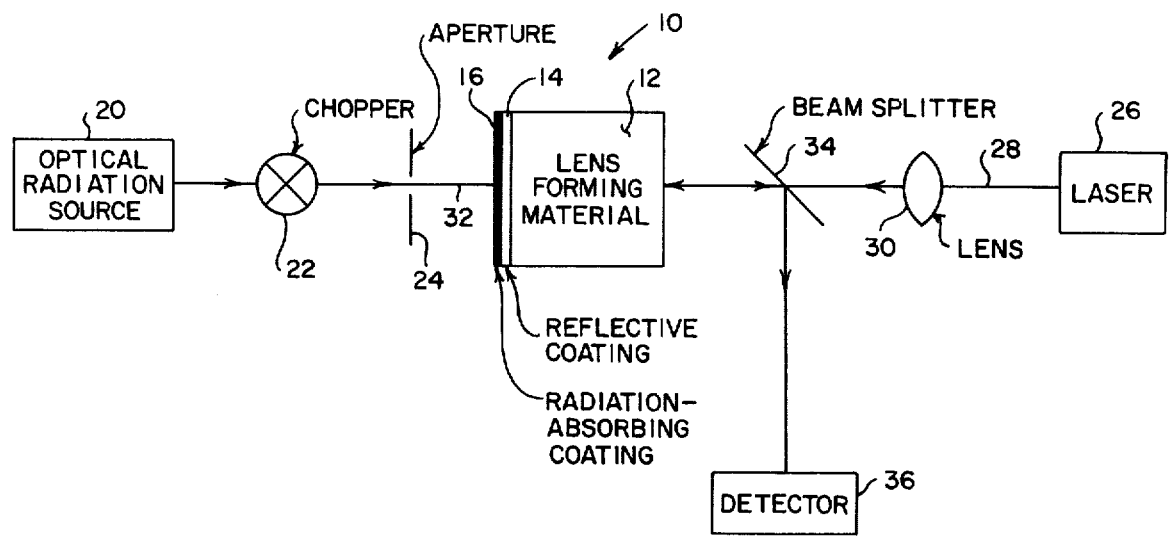
FIG. 1 is a block diagram showing an optical detector provided by the invention.

Referring now to FIG. 1, a lens-forming laminate or sensor 10 includes a lens-forming material 12, on one side of which is deposited a reflective coating 14. A radiation-absorbing coating 16 is deposited over the reflective coating 14, thereby forming a laminate comprised of the lens-forming material 12, reflective coating 14, and radiation-absorbing coating 16. It is important that the three materials 12, 14 and 16 be in thermally conductive contact with each other. Optical radiation to be detected is absorbed in the form of heat by the radiation-absorbing coating 16 and thermally conducted through the reflective coating 14 into the lens forming material 12, thereby forming a thermal lens which can be detected in a manner to be described below. An optical radiation source or heat source 20 provides the optical radiation to be detected. This optical radiation could have wavelengths ranging between the ultraviolet and far infrared wavelengths, although it is felt that the invention is particularly useful in detecting infrared wavelengths between 0.85 and 25 microns. Light from the optical radiation source 20 is periodically interrupted by a chopper 22 so that the optical radiation to be detected only intermittently irradiates the radiation-absorbing coating 16. An aperture-forming plate 24 is provided between the chopper 22 and the radiation-absorbing coating 16, the aperture defining a relatively small area on the radiation-absorbing coating which is to be intermittently irradiated by the optical radiation to be detected. A collimated light source which in this embodiment is a laser 26 is provided. A collimated light beam 28 from the laser 26 is focused by a focusing lens 30 at a point within the lens forming material 12, this focal point typically being at the interface between the reflective coating 14 and the lens-forming material 12 and along the axis of the optical radiation to be detected. The collimated light beam 28 is reflected backwardly along its axis from the reflective coating 14 to a beam splitter 34 from which it is reflected to an optical detector 36. It is important that the optical detector 36 have a detection area smaller than the cross section of the reflected beam so that it will be able to detect intensity changes resulting from beam defocusing by a thermal lens in the lens-forming material 12.

The lens forming material 12 is substantially transparent to the collimated light beam 28 and has a large change in refractive index with respect to a change in temperature $(dn/dt)$. This insures that maximum defocusing of the collimated light beam 28 is obtained for any given amount of heat generated in the radiation-absorbing coating 16. Examples of lens forming materials include piezoelectric or pyroelectric materials both of which are highly polarizable. Other lens-forming materials which could be utilized include hard plastics, rubbers, liquids having phase transitions at the temperature at which the thermal lens is to be formed, one example of which is carbon tetrachloride, and ferroelectric materials. Also, some materials may be cooled slightly to improve their lens-forming and dissipation characteristics. This would be especially true for a material in which a phase transition is desired at a temperature at which the thermal lenses are formed.

The reflective coating 14 could be a thin film of aluminum, silver, gold or any other material having high thermal conductivity and high reflectivity at the collimated light beam 28 wavelength. The radiation-absorbing coating 16 should provide maximum absorption at the wavelength or band of wavelengths of the radiation to be detected. It could be formed of lamp black, gold black, or platinum black. For a typical lens-forming laminate 10, the lens-forming material 12 could be 1/8" thick, the reflective coating 14 approximately 500 angstroms thick, and the radiation-absorbing coating 16 between 100-500 angstroms thick. The lens-forming material 12 is relatively thick in-order-to be able to dissipate heat surrounding and defining a thermal lens within the material. Thus, a thermal lens can be formed during the time the radiation-absorbing coating 16 is irradiated, and can be quickly dissipated when the optical radiation to be detected is blocked by the chopper 22. It has been found that a chopper 22 which passes radiation to be detected for approximately 1/3 of a time interval and blocks radiation for 2/3 of the time interval provides a means for detection of temperature changes as small as $10 \text{Exp}(-5)$ degrees K at intervals as closely spaced as 1 microsecond. The laser 26 providing the collimated light beam 28 could be a helium-neon laser having an output wavelength of about 600 nanometers. However, it is not necessary that a laser be utilized for the collimated light beam 28, and any other type of collimated light source could also be utilized. The optical detector 36 could be an ultra-sensitive photomultiplier/CCD system, or any other type of photon detector such as an optical multichannel analyzer (OMA). Although only one aperture 24 is shown, it should be appreciated that any number of apertures defining the optical radiation 32 to be detected could be utilized.

Figure 2:
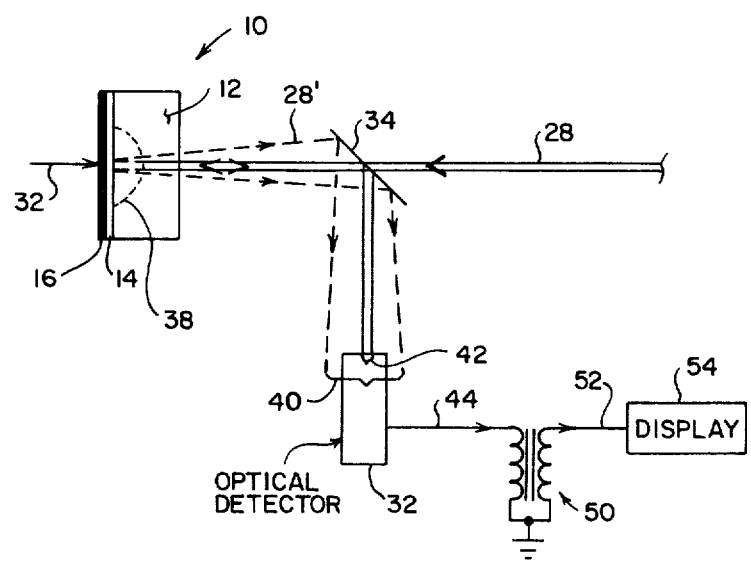
FIG. 2 is a ray trace diagram showing the path of the collimated light beam passing through a thermal lens.

The thermal lens detecting means can be further understood in reference to FIG. 2. In FIG. 2, the collimated light beam 28 passes through the beam splitter 34 and into the lens forming material 12. The optical radiation 32 to be detected heats the radiation-absorbing coating 16, the heat being thermally conducted through the reflective coating 14 and forming a thermal lens 38 in the lens-forming material 12. The dotted line defining the thermal lens 38 is merely outlining a volume within the lens-forming material 12 where the refractive index of the material is changed as a result of the heat generated by absorption of the optical radiation 32 to be detected. The collimated light beam 28' is spread or diffused as it enters the thermal lens 38, is reflected by the reflective coating 14, and spread again as it leaves the thermal lens 38. The thus-spread collimated light beam 28' is reflected downwardly by the beam splitter 34 and subtends an area one dimension of which is indicated by the parenthesis at 40. In the absence of a thermal lens 38 in the lens forming material 12, the collimated light beam is reflected by the beam splitter 34 to the optical detector 32 and subtends an area one dimension of which is shown by the parenthesis at 42. As one can appreciate, so long as the active area of the optical detector 32 is smaller than the area defined by the spread collimated light beam 28' then the output of the optical detector 32 will be lower than when it is irradiated by an unspread reflected collimated light beam. Thus, the output signal 44 from the optical detector 32 will vary from a maximum when there is no thermal lens in the lens forming material 12, to a value lower than the maximum when the thermal lens 38 is spreading the collimated light beam so that portions of the spread beam do not irradiate the optical detector 32.

Figure 3:
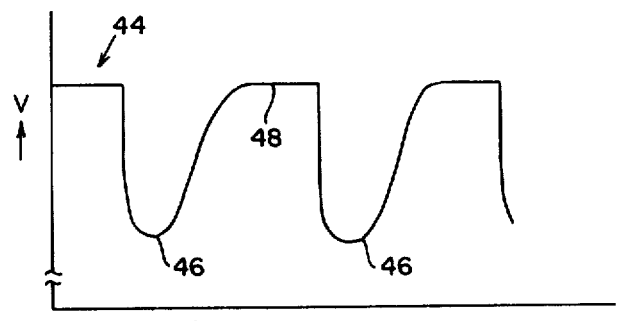
FIG. 3 is a waveform diagram of intensity versus time as seen by the optical detector.
Figure 4:
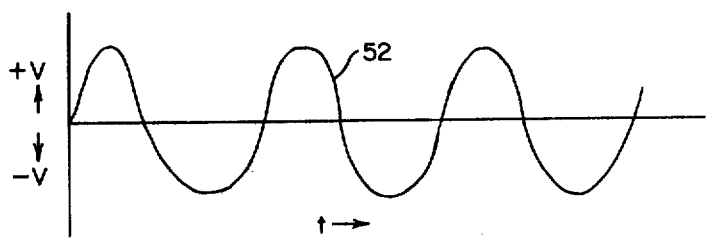
FIG. 4 is a waveform diagram of the output of the optical detector after having a DC bias removed.
Figure 5:
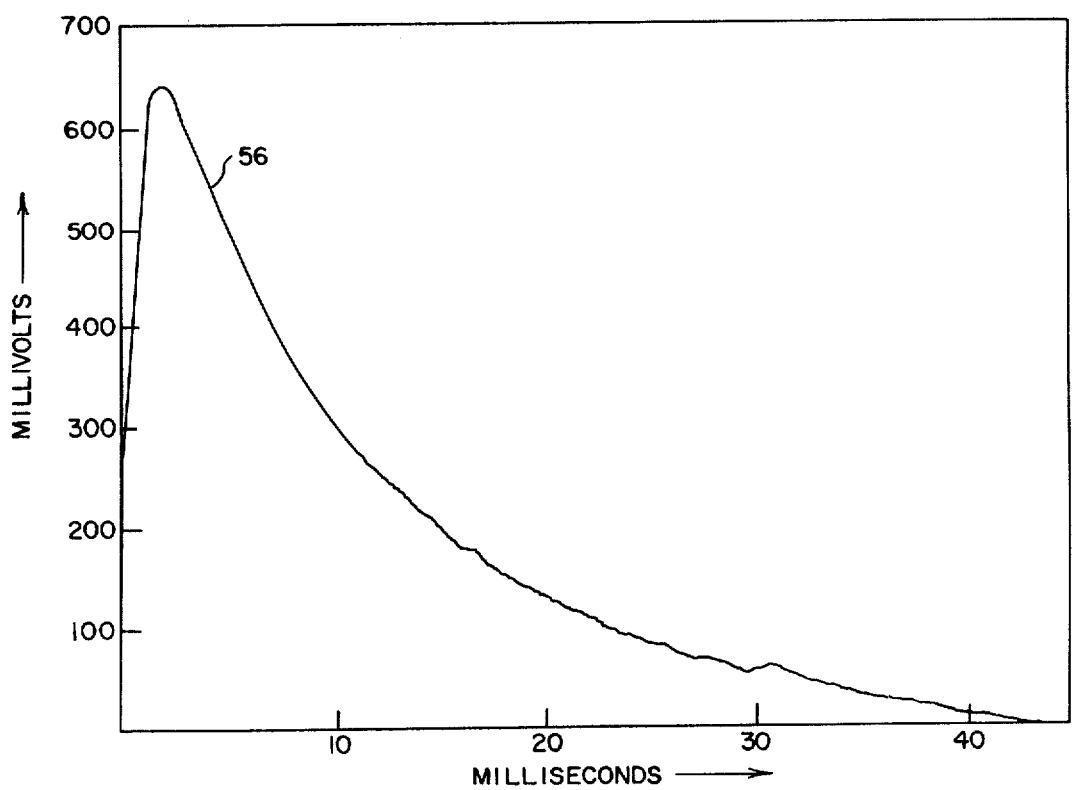
FIG. 5 is a graph showing voltage versus time of a voltage whose magnitude is related to formation and dissipation of the thermal lens.

The optical detector output 44 is shown in FIG. 3. In FIG. 3, the thermal lens is at a maximum as represented by the voltage shown at 46, and begins to dissipate until it is fully dissipated as represented by the voltage at 48. In order to eliminate the rather large DC bias corresponding to a voltage related to the voltage at 48, an AC coupling means 50 is provided, the output thereof being an alternating voltage 52 shown in FIG. 4. Thus, the magnitude of the alternating voltage 52 is directly related to the thermal lens 38 formed in the lens-forming material 12, and can be displayed by any suitable display means 54 which could be a vidicon, a strip recorder, or a display means associated with a processing computer. Characteristics of thermal lenses formed in the types of materials above-described can be seen in FIG. 5. In FIG. 5, an optical detector output voltage 56 is shown for a radiant input of 10 nanoseconds to a lens-forming material, the output voltage 56 being related to the formation and dissipation of the thermal lens formed therein.

Figure 6:
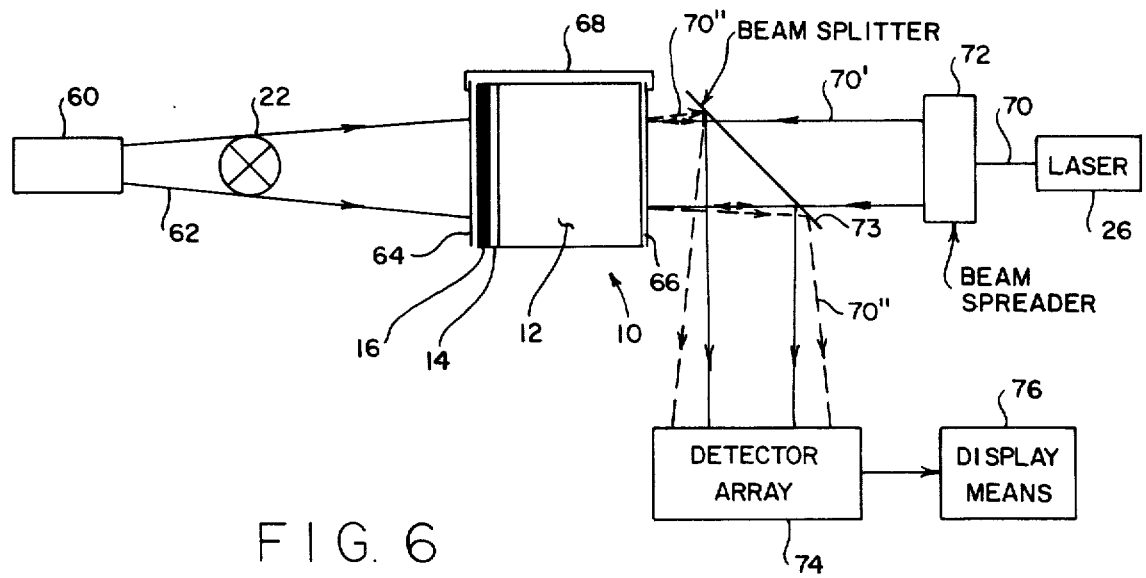
FIG. 6 is a block diagram of a second embodiment of the invention in which a detector array is provided.

A second embodiment of the invention is shown in FIG. 6. The chopper 22, lens-forming laminate 10 and the laser 26 are the same as in the first embodiment. However, in this embodiment the optical radiation from portions of an entire scene is to be detected. An optical radiation source 60 outputs a beam 62 of optical radiation to be detected. A first template 64 is provided between the radiation-absorbing coating 16 and the optical radiation source 60, the template 64 defining a plurality of openings, as will be explained below, so that selected portions of the optical radiation beam 62 to be detected can pass therethrough and irradiate the radiation-absorbing coating 16. A second template 66 is provided on the other side of the lens-forming material 12, the second template 66 defining a plurality of openings each of which corresponds to an opening in the first template 64. For reasons to be explained below, the two templates 64 and 66 are aligned with respect to each other by a holding bracket 68. A collimated light beam 70 from the laser 26 is provided to a conventional beam spreader 72 which outputs a spread beam 70' sufficiently large to irradiate an area defined by the openings in the second template 66. Thermal lenses in the lens-forming material 12 are formed in front of each of the openings in the first template 64 and are irradiated by light passing through corresponding openings in the second template 66. Light reflected by the reflective coating 14 defines a reflected beam 70" which is reflected by a beam splitter 73 to an optical detector array 74, the detector array 74 having a detector corresponding to each of the openings in the second template 66. Outputs from the detector array are provided to a display means 76. As one can appreciate, the reflected light beam 70" actually comprises a plurality of smaller light beams, each being formed by part of the spread beam 70' and defined by the various openings in the second template 66.

Figure 7:
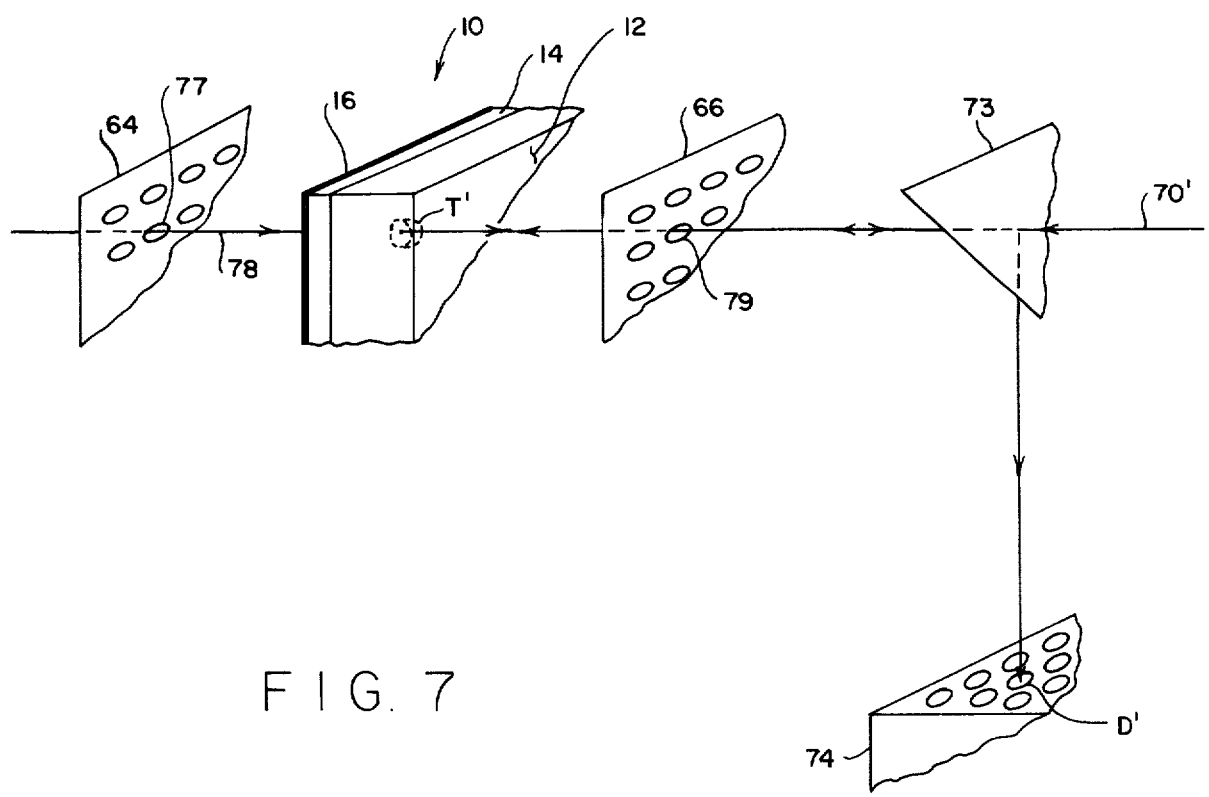
FIG. 7 is a perspective view of portions of the detector array shown in FIG. 6.

An exploded view of certain portions of the second embodiment shown in FIG. 6 can be seen in FIG. 7. Referring to FIG. 7, the first template 64 is shown in which a plurality of openings are provided. The number of openings can vary greatly. A typical opening for detection of infrared radiation would have a diameter between 0.05 millimeters and 0.1 millimeters, and be spaced-apart 0.5 millimeters with respect to each other. One of the openings 77 in the first template 64 allows a portion of the radiation to be detected to pass therethrough, that portion defining a light beam 78 which strikes the radiation-absorbing coating 16. As a result of conduction of heat through the radiation absorbing coating 16 and the reflective coating 14, a thermal lens T' is formed in the lens-forming material 12. This thermal lens T' is formed in a volume intersected by the axis of the light beam 78 passing through the first template 64. A portion of the collimated light beam 70' passing through the beam splitter 73 passes through an opening 79 in the second template 66, this opening being positioned so that the axis of the collimated light beam passing therethrough will be colinear with the axis of the optical radiation 78 passing through the corresponding opening 77 in the first template 64 and will intersect the thermal lens T' formed in the lens-forming material 12. The collimated light beam passing through the opening 79 in the second template 66 is reflected by the reflective surface 14 and passes backwardly along its axis through the opening 79. It is reflected downwardly by the beam splitter 73. The detector array 74 is positioned so that a corresponding detector element D' is intersected by the beam of collimated light passing through the opening 79 in the second template 66. Thus, a decrease in light intensity measured by the detector D' is related to spreading of the collimated light beam as it passes through the thermal lens T'. As in the first embodiment, the absence of a thermal lens T' will result in a maximum irradiation of the detector D', and the presence of a thermal lens T' will result in a spreading of the collimated light thereby reducing the intensity of light at the detector D'. In a corresponding manner, each of the other detectors comprising the detector array 74 corresponds to an opening in the second template 66 which, as previously explained, corresponds to an opening in the first template 64. Thus, each detector of the detector array 74 provides an output related to optical radiation passing through one of the plurality of openings in the first template 64.

Figure 8:
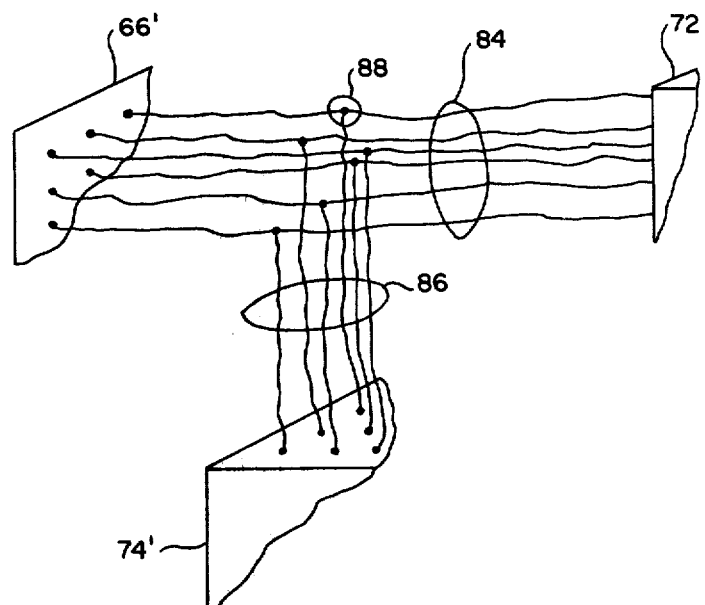
FIG. 8 is a partial perspective diagram of a third embodiment of the invention in which optical fiber bundles are utilized to transmit collimated light beams to the thermal sensor.
Figure 9:
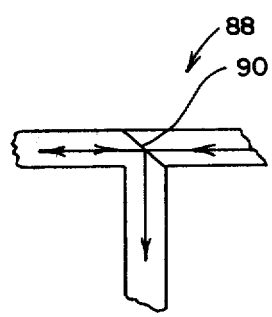
FIG. 9 is a schematic representation of one of the optical fiber bundles shown in FIG. 8 incorporating a beam splitting means for transmitting reflected light to an optical detector.

Referring to FIG. 8, a plurality of optical fiber bundles 84 are provided in a third embodiment of the invention. The output from the beam spreader 72 irradiates one end of the optical fiber bundles 84, the other end being terminated in a template 66' which is positioned with respect to the first template 64 in the same way as the second template 66 was positioned. The optical fiber bundles could be utilized whenever it would be impractical to orthogonally direct the output 70' from the beam spreader 72 at the second template 66. A second plurality of optical fiber bundles 86 is also provided, each of which is connected to one of the first plurality of optical fiber bundles. The second plurality of optical fiber bundles 86 is terminated in a detector array 74', the end of each of the optical fiber bundles being oriented so as to irradiate an individual optical detector. The detector array 74' again provides a plurality of outputs, each of which corresponds to one of the openings of the second template 66'. Refering to FIG. 9, an enlarged portion of an area designated as 88 in FIG. 8 is shown. Here, one of the optical fiber bundles is shown having a beam splitting means 90 provided therein. Light reflected from the beam splitting beams 90 is provided to one of the second optical fiber bundles 86.

It is theorized that if 80–90% of incident radiation is absorbed by the thermal lens-forming material having output characteristics as shown in FIG. 5, and a thermal lens is formed in the lens-forming material 12 by a circular chopper rotating at 20 Hz and having a 115° window, then the radiation to be detected will correspond to a continuous radiation level $28 \times 10 \, \text{Exp}(-9)$ watts over an absorption area of $10 \, \text{Exp}(-4)$ square centimeters. Using the above parameters, it is further theorized that responsivity will be approximately equal to $2 \times 10 \, \text{Exp}(-9)$ volts/watt-cm $\text{Exp}(2)$, the noise equivalent power will be $1.1 \times 10 \, \text{Exp}(-10)$ watts Hz $\text{Exp}(-\frac{1}{2})$, and D* will be equal to $9 \times 10 \, \text{Exp}(7)$ watt $\text{Exp}(-1)$Hz $\text{Exp}(-\frac{1}{2})$ cm.

Thus, it should be apparent from the foregoing description that a high sensitivity optical detector has been described in which optical radiation to be detected is directed to form one or more thermal lenses in a lens-forming material. Each thermal lens is probed by a collimated light beam which, after having passed through the thermal lens, has characteristics which are related to the optical radiation to be detected.

What is claimed is:

1. A broadband optical radiation detector comprising:
   a thermal lens-forming laminate comprising:
      a lens-forming material in which a thermal lens can be formed;
      a reflective coating in thermal contact with one surface of said lens-forming material; and
      a radiation-absorbing coating in thermal contact with said reflective coating;
   means for periodically irradiating said radiation-absorbing coating by optical radiation to be detected at a rate sufficiently slow that a thermal lens formed in said lens-forming material will substantially dissipate prior to formation of the next succeeding thermal lens; and
   means for detecting at least one thermal lens formed in said lens-forming material, said thermal lens being formed by a change in refractive index of said lens-forming material by heat transferred from said radiation-absorbing coating to said lens-forming material through said reflective coating, the characteristics of said thermal lens being related to said optical radiation to be detected.

2. The detector of claim 1 wherein said means for periodically irradiating comprises:
   means for alternately blocking and unblocking said optical radiation to be detected; and
   means for defining a predetermined area of said radiation-absorbing coating to be irradiated by said optical radiation to be detected.

3. The detector of claim 1 wherein said means for detecting comprises:
   means for generating a collimated light beam directed to irradiate a thermal lens formed in said lens-forming material; and
   means for determining the intensity of at least a portion of said collimated light beam after having passed through said thermal lens, said intensity being related to said optical radiation to be detected.

4. The detector of claim 3 wherein said collimated light beam is reflected from said reflective coating after having passed through said thermal lens, said means for determining comprises:
   a beam splitter located in said collimated light beam portion having passed through said thermal lens and reflected from said reflective coating; and
   means for measuring intensity changes in said collimated light beam portion reflected from said reflective coating and reflected by said beam splitter.

5. The detector of claim 4 wherein said means for measuring intensity comprises an optical detector having an output signal related to intensity of said collimated light beam reflected portion.

6. The detector of claim 5 wherein said means for measuring further comprises AC coupling means for removing DC biases from said optical detector output signal.

7. The detector of claim 3 wherein said means for generating a collimated light beam comprises a He-Ne laser.

8. The detector of claim 1 wherein said means for irradiating comprises:
   a first template forming a first plurality of openings, said first template being located so that optical radiation to be detected passes though said plurality of openings and irradiates said radiation absorbing-coating; and
   means for alternately blocking and unblocking said optical radiation to be detected, thereby resulting in a plurality of thermal lenses being formed in said lens forming material.

9. The detector of claim 8 wherein said means for detecting comprises:
   means for generating a collimated light beam directed to irradiate said plurality of thermal lenses formed in said lens-forming material; and
   means for determining the intensity of portions of said collimated light beam after having passed through said thermal lenses.

10. The detector of claim 9 wherein said means for generating comprises a second template forming a second plurality of openings, each of which corresponds to one of said plurality of thermal lenses, said second template being located in said collimated light beam so that collimated light passing through each of said second plurality of openings will form a light beam portion which will pass through a corresponding thermal lens in said lens forming material.

11. The detector of claim 10 wherein said means for detecting comprises:
- beam splitting means located in said collimated light beam portions having passed through said thermal lens in said lens-forming material; and
- means for measuring intensity changes of said collimated light beam portions reflected by said beam splitting means.

12. The detector of claim 11 wherein said means for measuring intensity comprises a plurality of optical detectors positioned so that one is in each of said collimated light beam portions reflected by said beam splitting means, the intensity profile of said collimated light beam portions being related to the intensity profile of said optical radiation to be detected.

13. The detector of claim 8 wherein said means for detecting comprises:
- a plurality of optical fiber bundles, one of which corresponds to each of said thermal lenses formed in said lens-forming material;
- means for generating a collimated light beam directed at one end of said plurality of optical fiber bundles;
- means for holding the other ends of said plurality of optical fiber bundles so that light radiating from each of said other ends will pass through its corresponding thermal lens; and
- means for determining the intensity of said light radiated from each of said plurality of optical fiber bundles after having passed through its corresponding thermal lens.

14. The detector of claim 13 wherein each of said plurality of optical fiber bundles comprises a beam splitting means, and said means for determining the intensity comprises means for measuring intensity changes of said collimated light having passed through said thermal lenses, reflected back through said thermal lenses to said optical fiber bundles other ends by said reflective coating, and reflected by said beam splitting means.

15. The detector of claim 14 wherein each of said plurality of optical fiber bundles comprises a second optical fiber bundle which is attached thereto so that light reflected by said reflective coating and said beam splitting means will enter said second optical fiber bundle, said means for determining the intensity comprises a plurality of optical detectors positioned so that each measures the intensity of light radiating from the end of said second optical fiber bundles.

16. The detector of claim 1 wherein said lens-forming material is a plastic material, rubber, liquid or ferroelectric material.

17. The detector of claim 1 wherein said reflective coating is silver, gold or aluminum.

18. The detector of claim 1 wherein said radiation-absorbing coating is lamp black, gold black, or platinum black.

19. A broadband infrared detector comprising:
- a thermal lens-forming sensor comprising a lens-forming material having first and second opposite, substantially parallel surfaces, a reflective coating formed on said first surface, and a radiation-absorbing coating formed on said reflective coating;
- means for alternately blocking and unblocking infrared radiation to be detected at a rate sufficiently slow to allow a thermal lens formed in said lens-forming material to substantially dissipate prior to formation of the next thermal lens;
- means for defining a predetermined pattern on said radiation-absorbing coating which is to be irradiated by said unblocked infrared radiation to be detected;
- means for generating a collimated light beam orthogonally directed at said lens-forming material second surface; and
- means for measuring intensity changes of a portion of said collimated light beam passing through a thermal lens formed by a change in refractive index of said lens forming-material by said infrared radiation to be detected.

20. The detector of claim 19 wherein said means for generating comprises means for dividing said collimated light beam into a plurality of smaller light beams, said smaller light beams defining a pattern on said lens-forming material second surface related to said predetermined pattern on said radiation-absorbing material so that each of said smaller light beams will pass through a thermal lens formed in said lens-forming material by infrared radiation irradiating said heat-absorbing material.

21. The detector of claim 20 wherein said means for dividing said collimated light beam into a plurality of smaller light beams comprises a plurality of optical fiber bundles between said collimated light generating means and said lens-forming material second surface, each of said optical fiber bundles carrying one of said smaller light beams.

22. The detector of claim 20 wherein said means for measuring intensity changes comprises:
- beam splitting means located in said plurality of smaller light beams, said beam splitting means reflecting light reflected by said lens-forming sensor reflecting coating; and
- a plurality of optical detectors positioned in a manner related to said predetermined pattern so as to be irradiated by portions of said smaller light beams having passed through thermal lenses formed in said lens-forming material by said infrared radiation to be detected.

23. The detector of claim 19 wherein said means for generating a collimated light beam comprises a laser.

24. A method for detecting optical radiation comprising the steps of:
- providing a thermal lens-forming sensor comprising a lens-forming material in which thermal lenses can be formed, one side of said material having a reflective coating in thermal contact therewith, and a radiation-absorbing coating in thermal contact with said reflective coating;
- intermittently irradiating said radiation-absorbing coating by said optical radiation to be detected at a rate sufficiently slow to allow a thermal lens formed in said lens-forming material to substantially dissipate prior to formation of the next thermal lens; and
- detecting a thermal lens formed by a change in refractive index of said lens forming material.

25. The method of claim 24 in which said detecting step comprises the steps of:

generating a collimated light beam directed to irradiate said thermal lens formed in said lens-forming material; and determining the intensity of at least a portion of said collimated light beam after having passed through said thermal lens and being reflected by said reflective coating.

26. The method of claim 25 wherein said determining step comprises the steps of:
inserting a beam splitter in said collimated light beam after having been reflected by said reflective coating; and
measuring intensity changes of said collimated light beam reflected by said beam splitter.

* * * * *